(12) United States Patent
Hacker et al.

(10) Patent No.: US 10,123,892 B2
(45) Date of Patent: Nov. 13, 2018

(54) SYSTEM FOR LOADING A COLLAPSIBLE HEART VALVE HAVING A LEAFLET RESTRAINING MEMBER

(71) Applicant: St. Jude Medical, Cardiology Division, Inc., St. Paul, MN (US)

(72) Inventors: Dean Hacker, Maple Grove, MN (US); Mary Johnson, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 184 days.

(21) Appl. No.: 15/161,411

(22) Filed: May 23, 2016

(65) Prior Publication Data

US 2016/0346106 A1 Dec. 1, 2016

Related U.S. Application Data

(60) Provisional application No. 62/167,420, filed on May 28, 2015.

(51) Int. Cl.
*A61F 2/95* (2013.01)
*A61F 2/24* (2006.01)

(52) U.S. Cl.
CPC ............... *A61F 2/95* (2013.01); *A61F 2/243* (2013.01); *A61F 2/2415* (2013.01); *A61F 2/2418* (2013.01); *A61F 2/2436* (2013.01); *A61F 2002/9522* (2013.01)

(58) Field of Classification Search
CPC ........ A61F 2/95; A61F 2/2436; A61F 2/2418; A61F 2/243; A61F 2/2415; A61F 2002/9522
See application file for complete search history.

(56) References Cited

U.S. PATENT DOCUMENTS

| 8,562,663 | B2 | 10/2013 | Mearns et al. |
| 9,192,469 | B2 | 11/2015 | Mearns et al. |
| 9,414,914 | B2 | 8/2016 | Duffy et al. |
| 9,414,917 | B2 | 8/2016 | Young et al. |

(Continued)

FOREIGN PATENT DOCUMENTS

| WO | 2009091509 A1 | 7/2009 |
| WO | 2013016513 A1 | 1/2013 |

OTHER PUBLICATIONS

International Search Report and Written Opinion for Application No. PCT/US2016/033703 dated Aug. 3, 2016.

*Primary Examiner* — John C Hong
(74) *Attorney, Agent, or Firm* — Lerner, David, Littenberg, Krumholz & Mentlik, LLP

(57) ABSTRACT

An assembly for loading a self-expanding prosthetic heart valve into a delivery device, includes a compression member having a longitudinal axis, a first open end with a first diameter, a second open end with a second diameter less than the first diameter, and a wall decreasing in diameter from the first open end to the second open end, a support member having a longitudinal axis, a base and a recess extending along the longitudinal axis and adapted to receive an end of the valve, the support member and the compression member being movable between an initial position and an operative position, and a substantially tubular restrainer disposed within the support member and, in the operative position of the compression member and the support member, defining a passageway for accepting a portion of the delivery device and leaflets of the valve when the valve is assembled on the support member.

11 Claims, 15 Drawing Sheets

(56) References Cited

U.S. PATENT DOCUMENTS

| | | |
|---|---|---|
| 2007/0239271 A1 | 10/2007 | Nguyen |
| 2014/0331475 A1 | 11/2014 | Duffy et al. |
| 2015/0081011 A1 | 3/2015 | Young et al. |
| 2016/0278955 A1 | 9/2016 | Liu et al. |

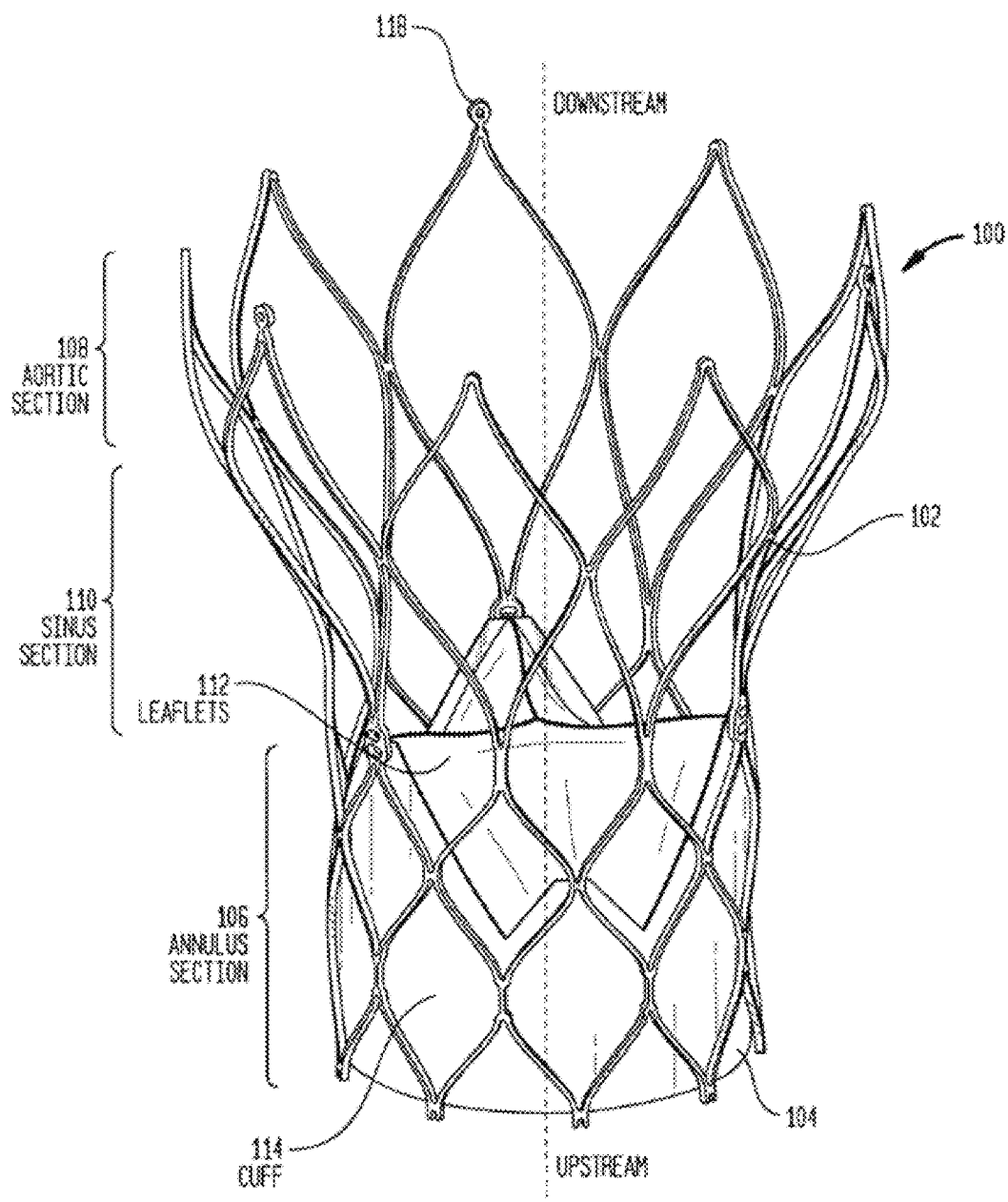

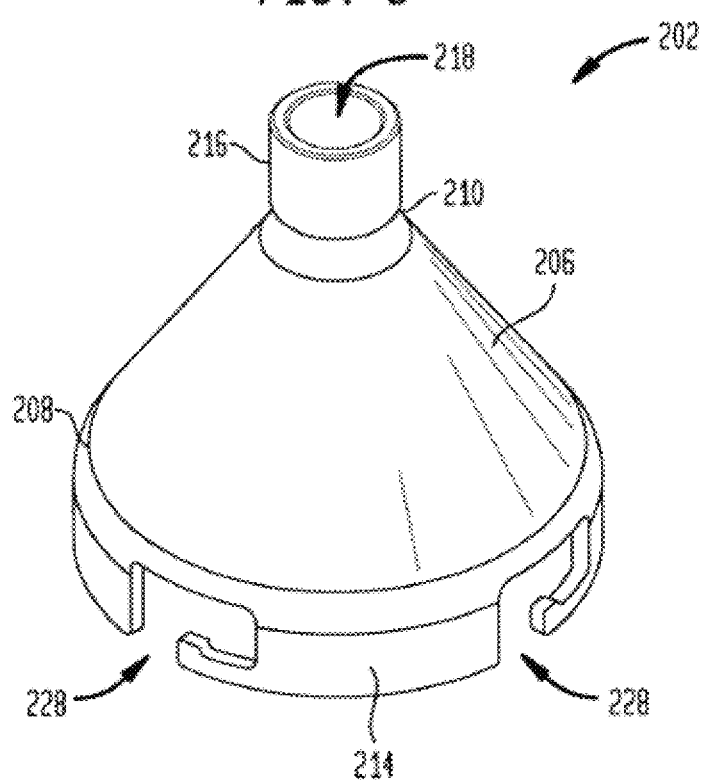

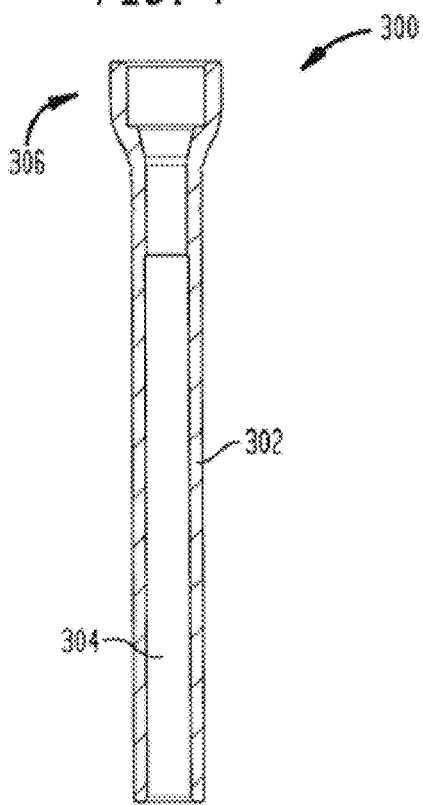
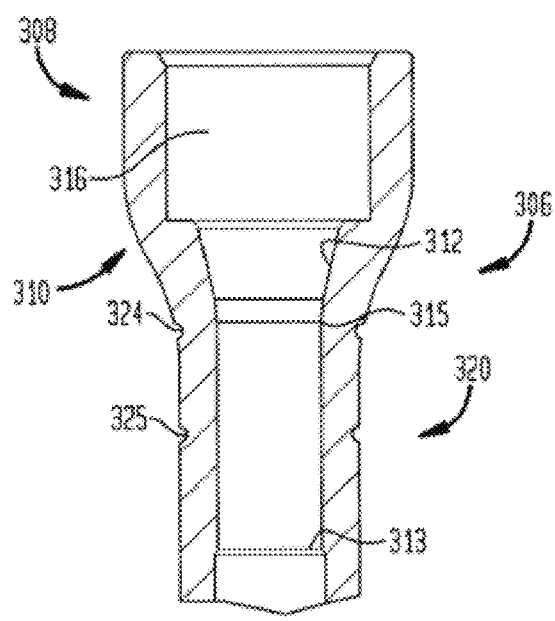

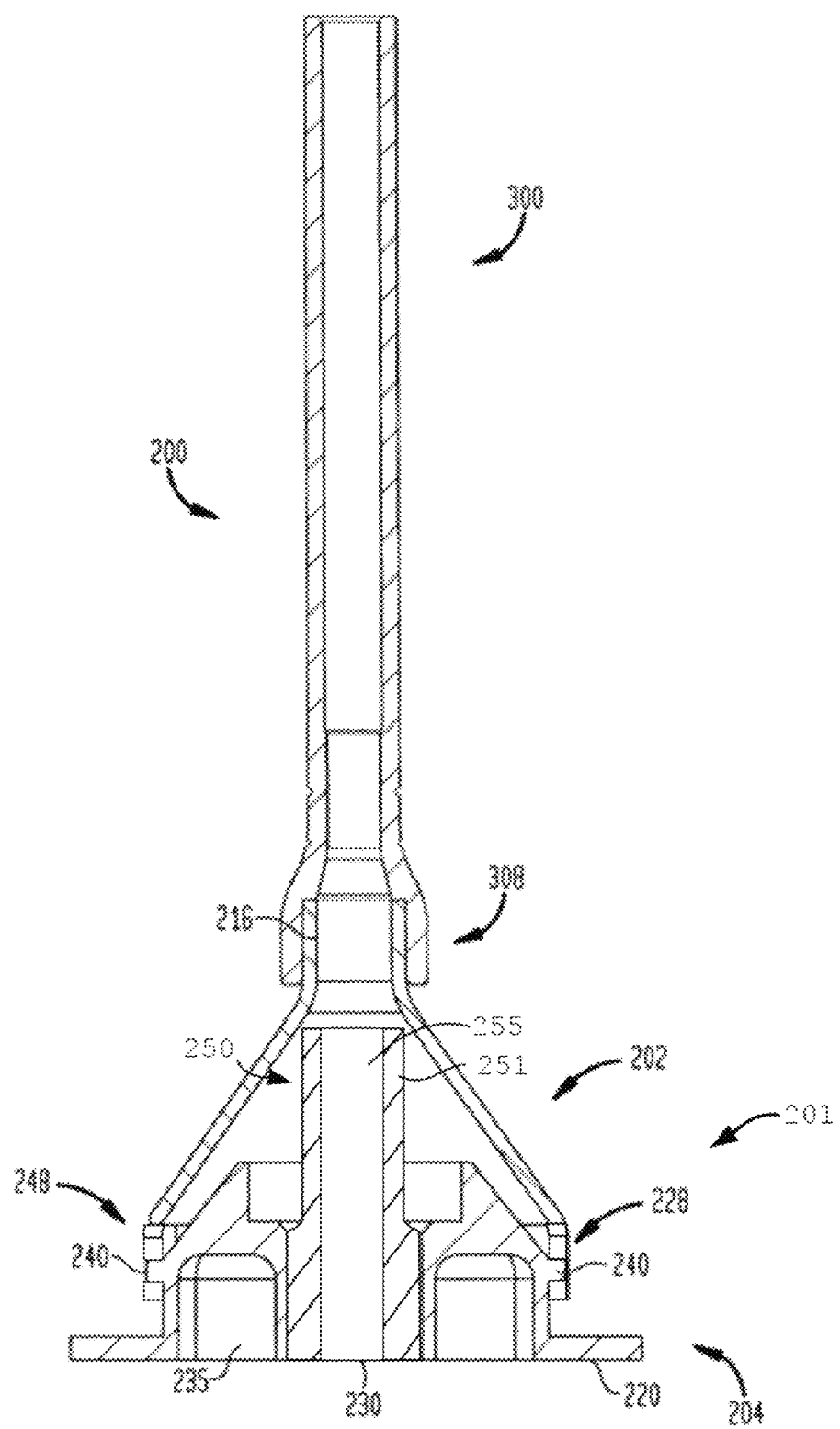

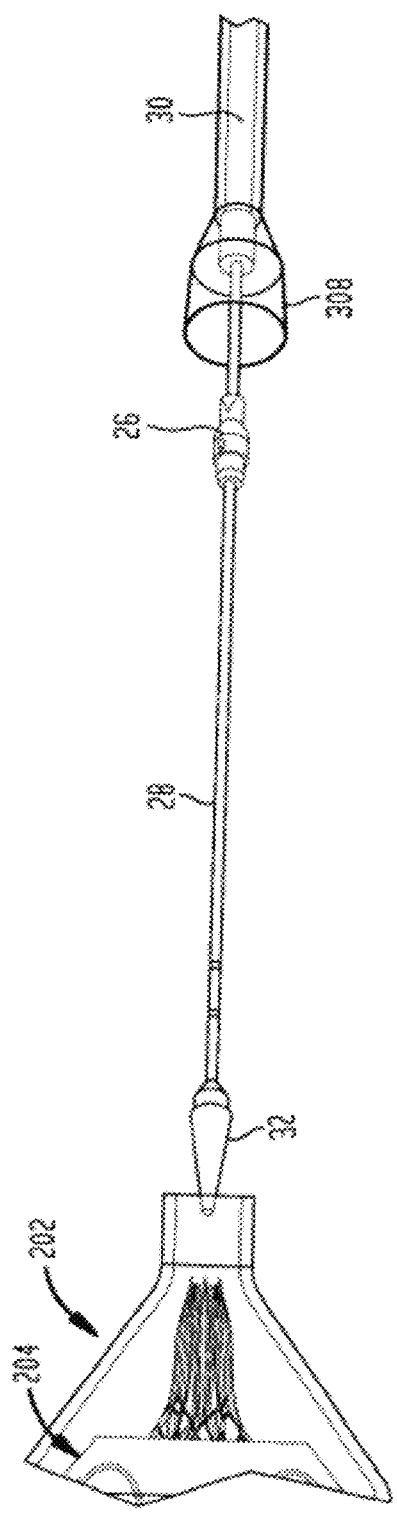

SYSTEM FOR LOADING A COLLAPSIBLE HEART VALVE HAVING A LEAFLET RESTRAINING MEMBER

CROSS-REFERENCE TO RELATED APPLICATIONS

The present application claims the benefit of the filing date of U.S. Provisional Patent Application No. 62/167,420 filed May 28, 2015, the disclosure of which is hereby incorporated herein by reference.

BACKGROUND OF THE INVENTION

The present disclosure relates to prosthetic heart valve implantation and, more particularly, to assemblies and methods for loading a self-expanding collapsible heart valve into a delivery device.

Prosthetic heart valves may be formed from biological materials such as harvested bovine valves or pericardial tissue. Such valves are typically fitted within a stent, which may be inserted into the heart at the annulus of the compromised native valve to replace the native valve. To perform such insertion procedure using a minimally invasive technique, it is typically necessary to compress the stent to a reduced diameter for loading into the delivery device.

In the case of valves formed from biological materials, the stented valve is preferably preserved in the open condition for storage as compression of the valve material for extended periods compromises the integrity of the biological valve. It is therefore necessary to crimp the valve, or reduce its diameter for loading in the delivery device, in the operating arena.

Some crimping devices and methods for collapsing a stented valve, including direct radial assemblies, have proven to be unsatisfactory as they include bulky assemblies, are difficult to master, are time consuming, impart undue stress on the stented valve, or exhibit other undesirable qualities. Moreover, it is sometimes difficult to securely engage the stent to the retaining element of the delivery device. It would therefore be beneficial to provide a device and method for collapsing a stented bioprosthetic heart valve using apparatus and techniques that overcome the deficiencies of conventional devices. In addition, such devices and methods could be useful in the loading of the collapsed stented valve into a minimally invasive delivery device.

BRIEF SUMMARY OF THE INVENTION

In some embodiments, an assembly for loading a self-expanding prosthetic heart valve into a delivery device, includes a compression member having a longitudinal axis, a first open end with a first diameter, a second open end with a second diameter less than the first diameter, and a wall decreasing in diameter from the first open end to the second open end, the wall defining an open space adapted to receive the valve, a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member, and a substantially tubular restrainer disposed within the support member and, in the operative position of the compression member and the support member, defining a passageway for accepting a portion of the delivery device and leaflets of the valve when the valve is assembled on the support member.

In some embodiments, a method for loading a self-expanding prosthetic heart valve into a delivery device includes (a) inserting the heart valve in a support member and about a substantially tubular restrainer, the support member having a longitudinal axis, a base and a recess extending along the longitudinal axis and adapted to receive an end of the valve, and the substantially tubular restrainer defining a passageway configured to obstruct movement of leaflets of the heart valve, and (b) moving the portion of the delivery device through the passageway.

BRIEF DESCRIPTION OF THE DRAWINGS

Various embodiments of the present loading assembly are disclosed herein with reference to the drawings, wherein:

FIG. 4 is a perspective view of a self-expanding prosthetic heart valve;

FIG. 5 is a perspective view of a compression member in accordance with an embodiment of the present invention;

FIG. 7 is a longitudinal cross-sectional view of a constricting member in accordance with an embodiment of the present invention;

FIG. 8 is an enlarged longitudinal cross-sectional view of an end section of the constricting member of FIG. 7;

FIG. 9 is a longitudinal cross-sectional view of a loading assembly in accordance with an embodiment of the present invention, including the compression member of FIG. 5, the support member of FIG. 6A, and the constricting member of FIG. 7;

FIGS. 10-19 illustrate the steps of a method for loading a prosthetic heart valve into a delivery device using the loading assembly of FIG. 9;

DETAILED DESCRIPTION

Figure 1:
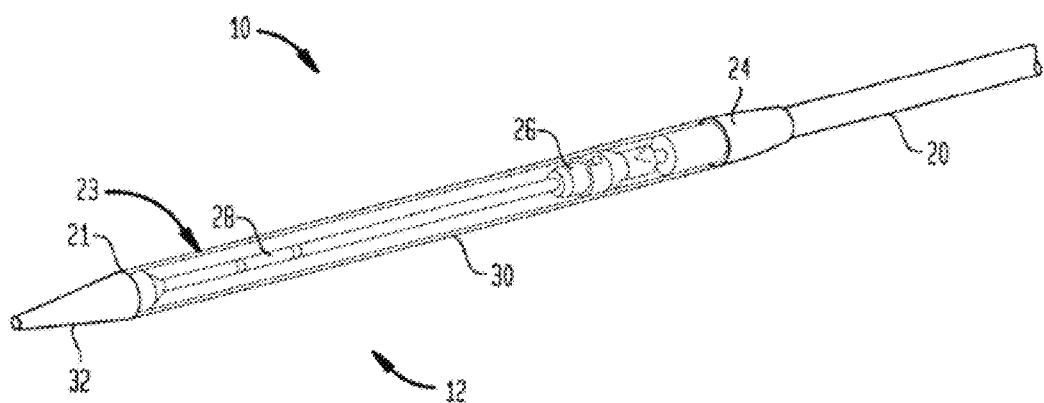
FIG. 1 is a perspective view of the distal portion of a delivery device.

Embodiments of the presently disclosed loading assemblies are described herein in detail with reference to the drawing figures, wherein like reference numerals identify similar or identical elements. In the description which follows, the term "proximal" refers to the end of the loading assembly, delivery device or portion thereof, which is closest to the operator during use, while the term "distal" refers to the end of the loading assembly, delivery device or portion thereof, which is farthest from the operator during use.

The present disclosure relates to assemblies and methods for loading a self-expanding stent or a collapsible prosthetic heart valve into a minimally invasive delivery device. An exemplary minimally invasive delivery device 10 is illustrated in FIGS. 1 and 2.

Figure 2:
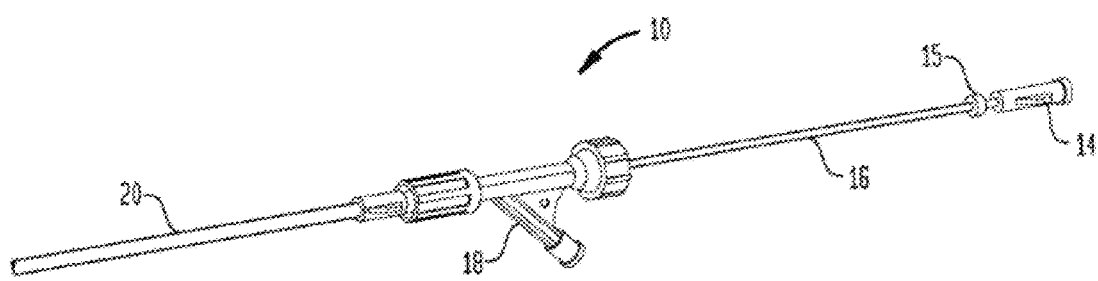
FIG. 2 is a perspective view of the proximal portion of the delivery device of FIG. 1.

As seen in FIGS. 1 and 2, an exemplary delivery device 10 for transfemoral delivery of a collapsible prosthetic heart valve (or other types of self-expanding collapsible stents) has a catheter assembly 12 for delivering the heart valve to and deploying the heart valve at a target location. The catheter assembly 12 includes a compartment 23 defined between an atraumatic tip 32 of the delivery device 10 and a retaining element 26. A support shaft 28 is connected between tip 32 and retaining element 26 and defines the length of compartment 23. A distal sheath 30 is slidably arranged relative to the compartment 23 so that, in a distalmost or closed position in which the distal end 21 of the sheath abuts atraumatic tip 32, the sheath covers the prosthetic heart valve and retains it for delivery to the target site, and in a proximal or open position in which the distal end 21 of the sheath is spaced from the atraumatic tip 32, the sheath uncovers the prosthetic heart valve for deployment at the target site.

An inner tube 16 having a lumen therethrough extends from a hub 14 at or near its proximal end to a distal end which may be connected to retaining element 26. Optionally, the distal end of inner tube 16 may extend through retaining element 26 and support shaft 28 for connection to atraumatic tip 32. In either arrangement, the distal end of inner tube 16 is connected to compartment 23 so as to define a fixed distance between hub 14 and the compartment. The lumen through inner tube 16 is sized to slidingly receive a guidewire (not shown) for use in guiding the delivery device to the target site. At its proximal end, inner tube 16 may be provided with a hemostasis valve (not shown) for preventing, or at least hindering, blood flow out from the inner tube.

Hub 14 is adapted for connection to another system or mechanism, such as an operating handle (not shown) for displacing the distal sheath 30. Mechanisms for displacing the distal sheath 30 between its proximal and distal positions are described in International Patent Application Publication No. WO/2009/091509, the disclosure of which is hereby incorporated by reference herein. A retaining ring 15 may be mounted on the inner tube 16 near hub 14.

Catheter assembly 12 further includes an outer shaft 20 which is connected at its distal end through a tapered transition member 24 to the proximal end of distal sheath 30, and at its proximal end to the operating handle (not shown). A Y-connector 18 may also be connected at the proximal end of outer shaft 20, and may include a hemostasis valve for hindering blood flow out from between the inner tube 16 and the outer shaft 20. The Y-connector 18 may also be coupled to a fluid source for flushing the outer shaft 20, injecting contrast media during a prosthetic valve implantation procedure, and the like.

Figure 3:
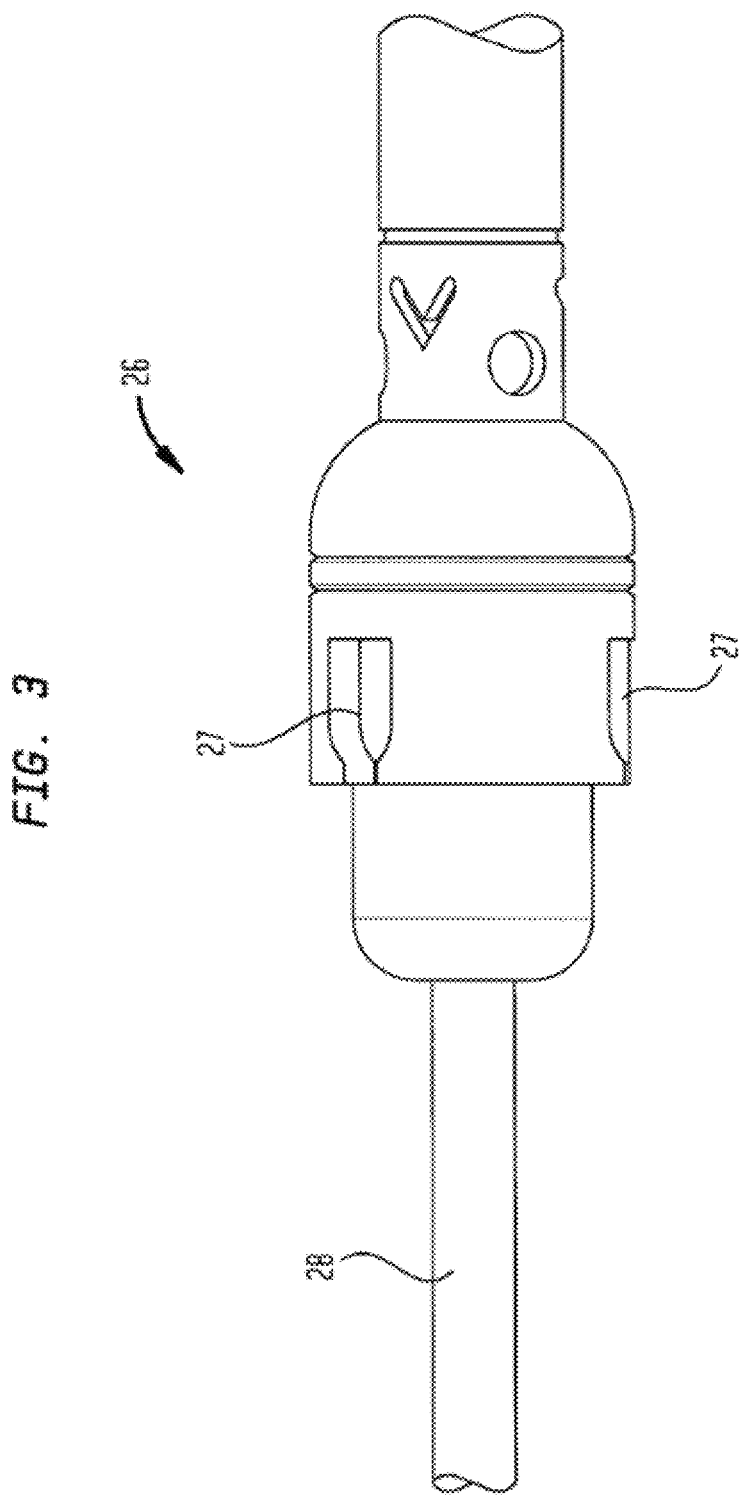
FIG. 3 is an enlarged side view of a retaining element of the delivery device shown in FIGS. 1 and 2.

As shown in FIG. 3, the retaining element 26 may include a plurality of recesses 27 located around its periphery. The recesses 27 are spaced apart from one another and each is sized and shaped to receive a tab or retainer on one end of the prosthetic heart valve to maintain the prosthetic heart valve in assembled relationship with the delivery device 10, to minimize longitudinal movement of the prosthetic heart valve relative to the delivery device during unsheathing and resheathing procedures, to help prevent rotation of the prosthetic heart valve relative to the delivery device as the delivery device is advanced to the target site and during deployment, and to maintain the alignment of the stent cells and prevent them from becoming tangled.

FIG. 4 shows a conventional bioprosthetic valve 100 designed to replace a native aortic valve. The valve 100 has a collapsed condition and an expanded condition and may be formed from a collapsible framework or stent 102, with a valve assembly 104 internally connected to the stent. The stent 102 may be formed from any suitable biocompatible material, such as nitinol or any other suitable elastic or shape memory material, and may include an annulus section 106, an aortic section 108, and a sinus section 110 located between the annulus section and the aortic section. The aortic section 108 may have a larger cross-section than the annulus section 106. The valve assembly 104 conventionally includes a plurality of leaflets 112 and a cuff 114 attached to the stent 102. The leaflets 112 and the cuff 114 may be formed from a biocompatible polymer, from natural tissue such as bovine or porcine pericardial tissue, or from other appropriate biocompatible materials. The valve assembly 104 is preferably connected to the stent 102 generally within the annulus section 106. The valve 100 may include a plurality of tabs or retainers 118 at spaced positions around one or both ends of the stent 102 for engagement with the retaining element 26 of the delivery device 10 as described above. The retainers 118 may also be utilized to collapse the valve 100 for loading into the delivery device 10, as will be discussed below.

The valve 100 is preferably stored in its expanded or open condition as the bioprosthetic valve assembly 104 may be compromised by storage in a collapsed condition for extended periods of time. As such, it is necessary to crimp the valve 100 into a collapsed condition of reduced cross-section for loading into the delivery device 10 at the latest possible time prior to the surgical implantation procedure. In order to effectively limit the time period the valve 100 is collapsed, the crimping process is preferably conducted in the operating arena by the surgeon, interventional cardiologist or surgical assistant using a specialized assembly.

Figure 6A:
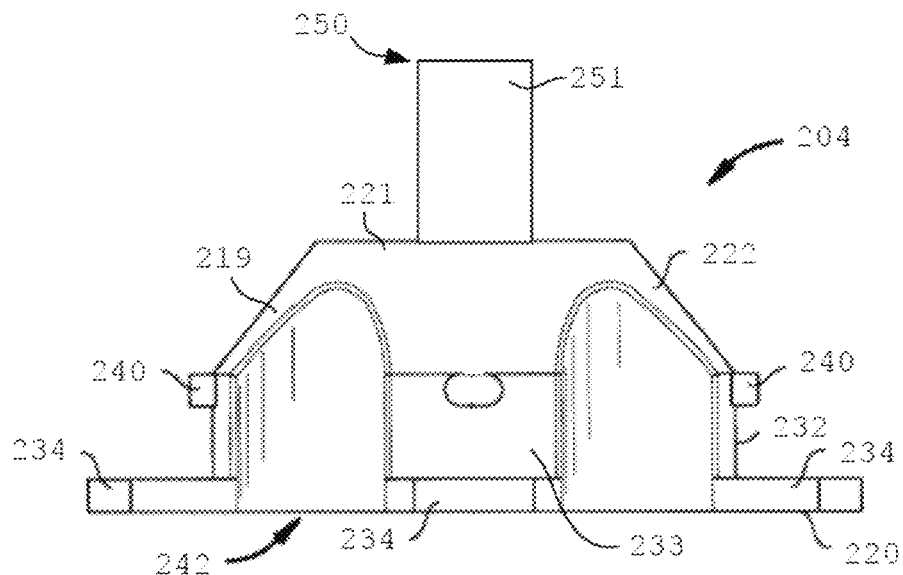
FIG. 6A is a perspective view of a support member in accordance with an embodiment of the present invention.
Figure 6B:
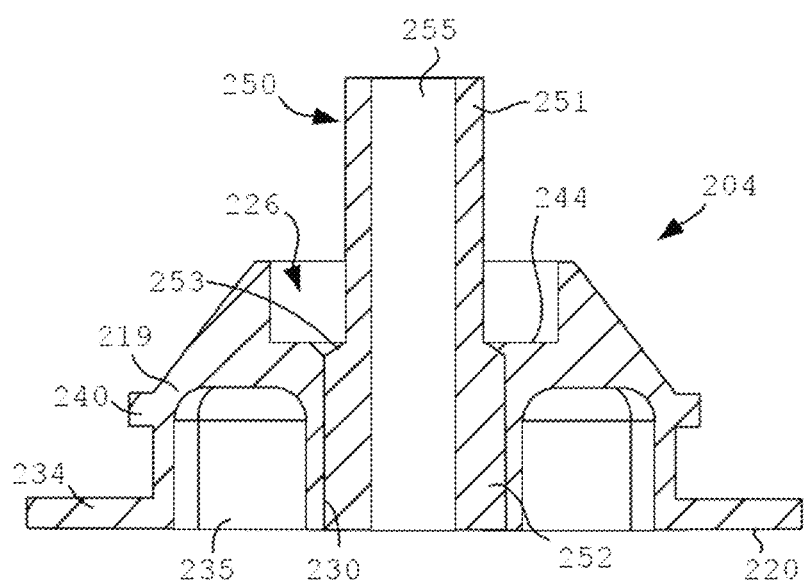
FIG. 6B is a cross-sectional view of the support member of FIG. 6A.

FIGS. 5 and 6A-B illustrate a loading assembly 200 according to one embodiment of the present invention, the loading assembly generally including a compression member 202 and a support member 204 adapted to be coupled to one another. The compression member 202 includes a funnel 206 having a substantially frusto-conical shape with a large diameter at a first end 208 and a smaller diameter at a second end 210. The diameter of the funnel 206 may decrease uniformly from the first end 208 to the second end 210 to compress the valve 100 as it is advanced through the compression member 202. The compression member 202 is preferably made of a substantially rigid material, and may be wholly or partly made of a transparent plastic, such as polycarbonate or acrylic, to allow viewing of the valve 100 during loading.

The compression member 202 may further include an annular rim 214 extending from the first end 208 of the funnel 206 for joining the compression member to the support member 204 as described below. The rim 214 may include a plurality of slots 228 disposed around its outer periphery. While the drawings show slots 228 that are substantially P-shaped, the slots may have any other shapes suitable for securely holding the compression member 202 to the support member 204. The rim 214 may include four such slots 228, or more or less than four. Regardless of the number or slots 228, adjacent slots are preferably spaced equidistantly from each other.

The compression member 202 also may include a tubular extension 216 projecting from the second end 210 of the funnel 206. The tubular extension 216 has an opening 218 therethrough in communication with the interior of funnel 206. The opening 218 is sized and shaped to receive the distal sheath 30 of the delivery device 10 therein. The cross-section of the tubular extension 216 is preferably substantially circular, but may be oblong, oval, elliptical, or polygonal.

With reference to FIGS. 6A-B, support member 204 is preferably made in whole or in part of a substantially rigid material, and includes a body 219 having a substantially flat or planar bottom support surface 220 and a top end 221. Body 219 has an outer wall 232 and a generally cylindrical bore 230 extending therethrough. A recess 226 extends downwardly from the top end 221 of body 219 concentrically with bore 230 so as to define an annular ridge 244 at a spaced distance from the top end (e.g., approximately one third of the distance between top end 221 and support surface 220). Recess 226 has a diameter and a depth defined by ridge 244 sufficient to receive at least a portion of the annulus section 106 of the stent 102 in an expanded condition.

The outer wall 232 of body 219 does not extend continuously around the body, but rather is interrupted by a plurality of inwardly curved indentations 242 which divide the outer wall into a plurality of wall segments 233. Indentations 242 facilitate the grasping of support member 204. Between indentations 242, that is, in the space between outer wall segments 233 and bore 230, body 219 may include a plurality of recesses 235 extending inwardly from the bottom support surface 220. Recesses 235 reduce the mass of body 219 and facilitate the manufacturing process by eliminating excessively thick portions of the body.

The outer wall segments 233 of body 219 do not extend all the way to the top end 221 of the body, but rather terminate at their top ends at a continuous wall 222 oriented at an oblique angle to the outer wall 232. At their bottom ends, outer wall segments 233 each include a radially projecting supporting plate 234, the bottom surfaces of which are substantially coplanar with the bottom support surface 220 of body 219. At least one pin 240 may protrude radially outward from each outer wall segment 233. Pins 240 are preferably spaced a sufficient distance from supporting plates 234 and sized and shaped to be received in the slots 228 of the compression member 202 to join the compression member and the support member 204 together. When joined together, the compression member 202 and the support member 204 collectively define a partial loading assembly 201.

Support member 204 further includes a leaflet restrainer 250 in the shape of a substantially cylindrical tube having a passageway 255 extending lengthwise therethrough. In the example shown, restrainer 250 includes a first portion 251 and a second portion 252, the second portion having a larger outer diameter than the first portion. An inclined surface 253 may be interposed between the smaller diameter first portion 251 and the larger diameter second portion 252, and may mate with a similarly inclined surface in body 219. Second portion 252 may be assembled in bore 230 and held in place therein by a press fit, adhesive, ultrasonic welding or other known techniques. Alternatively, restrainer 250 may be formed integrally with body 219. In still other examples, restrainer 250 may be separable from body 219, and may include clips or other fasteners for coupling to and decoupling from body 219 as desired. In this assembled position, restrainer 250 defines a generally cylindrical passageway 255 through support member 204 and projecting upwardly from annular ridge 244, the diameter of passageway 255 being constant along the length of restrainer 250. Passageway 255 is sized and shaped to receive at least a portion of the tip 32 of delivery device 10 therein, as will be evident from the description below.

FIGS. 7 and 8 illustrate a constricting member 300 designed to minimize the flaring of the distal end 21 of the distal sheath 30 during loading of a prosthetic heart valve into the compartment 23 of delivery device 10. The constricting member 300 may be wholly or partly made of a transparent plastic, such as polycarbonate or acrylic, to allow viewing of the delivery device 10 during loading and includes a tubular portion 302 having a central lumen 304 sized and shaped to slidingly receive at least the distal sheath 30 of the delivery device 10.

As seen in FIG. 8, at one end 306, the constricting member 300 may have an enlarged head 308 with a counterbore 316 formed therein. The counterbore 316 may have a diameter that is larger than the diameter of lumen 304, and in particular, may be sized and shaped to receive the tubular extension 216 of the compression member 202. Preferably, the diameter of counterbore 316 is only slightly larger than the outer diameter of the tubular extension 216 so as to create a friction fit therebetween.

Between the tubular portion 302 and the enlarged head 308, constricting member 300 may have a tapered portion 310. In particular, tapered portion 310 may have an inner surface 312 that tapers from a larger diameter at its end adjacent the counterbore 316 to a smaller diameter at its other end to help compress valve 100 further during loading into delivery device 10.

The constricting member 300 may further include a transition portion 320 disposed between the tapered portion 310 and the tubular portion 302. The transition portion 320 may have a substantially constant inner diameter sized and shaped to receive at least the distal sheath 30 of the delivery device 10. The inner diameter of the transition portion 320 may be slightly smaller than the diameter of lumen 304 and slightly larger than the outer diameter of the distal sheath 30 in order to substantially prevent or minimize the flaring of the distal end 21 of the distal sheath 30 while the valve 100 is being loaded in the delivery device 10, as discussed in detail below. The larger diameter of the lumen 304 allows a user to easily slide the constricting member 300 over the distal sheath 30 of the delivery device 10. In a variant hereof, the transition portion 320 may have an inner diameter that tapers downwardly from a slightly larger diameter at an end 313 thereof to a slightly smaller diameter at an end 315 thereof to accommodate small variations in the outer diameter of the distal sheath 30.

An annular groove or other indicator line 324 may extend partly or entirely around the outer periphery of the constricting member 300 at the junction between the tapered portion 310 and the transition portion 320. Another annular groove or indicator line 325 may extend partly or entirely around the outer periphery of the constricting member 300 at a spaced distance from the first line 324. Lines 324 and 325 mark the area in which the user should place the distal end 21 of the distal sheath 30 during the loading procedure. As discussed in detail below, using the constricting member 300 to help load the valve 100 into the delivery device 10 reduces the loading forces (i.e., the forces required to load the valve into the delivery device) and reduces flaring of the distal end 21 of the distal sheath 30.

FIG. 9 shows an assembled loading assembly 200 including the compression member 202 of FIG. 5, the support member 204 of FIGS. 6A and B and the constricting member 300 of FIG. 7. As seen in FIG. 9, the constricting member 300 is connected by its enlarged head 308 to the tubular extension 216 of the compression member 202, and the compression member 202 is locked to the support member 204. To lock the compression member 202 to the support member 204, the pins 240 of the support member are inserted into the slots 228 of the compression member, and the compression member is turned relative to the support member to slide the pins toward the closed ends of the slots. Hence, the pins 240 and the slots 228 together form a locking mechanism 248. Rather than the engagement of the pins 240 in the slots 228, it is contemplated that any other known locking mechanisms may be employed to securely lock the compression member 202 to the support member 204.

Figure 10:
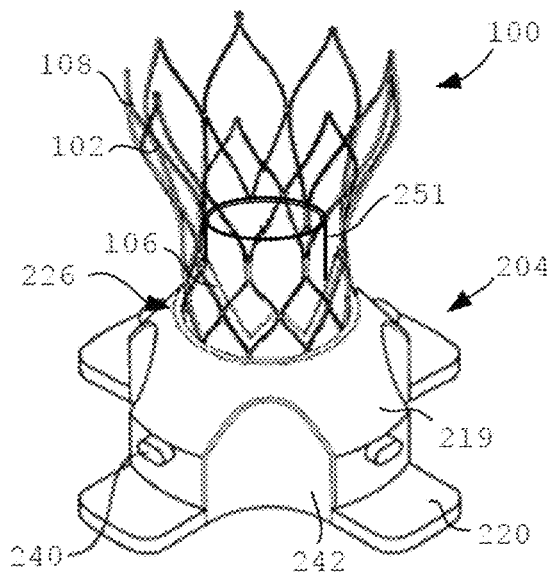

As seen in FIGS. 10-19, the loading assembly 200 may be used to load the collapsible prosthetic heart valve 100 into a delivery device 10. As shown in FIG. 10, with the support member 204 on a flat surface, at least a portion of the annulus section 106 of the stent 102 may be placed within the recess 226 of the support member until the end of the stent contacts ridge 244. In this position, an upper portion of restrainer 250 extends through the leaflets 112 of valve 100. Specifically, first portion 251 of restrainer 250 extends through annulus section 106 of valve 100 and through the junction of leaflets 112, pushing the leaflets to an open (e.g., not coapting but spaced apart) position. Leaflets 112 are thus kept from coapting with one another, creating a clear passageway through valve 100.

Figure 11:
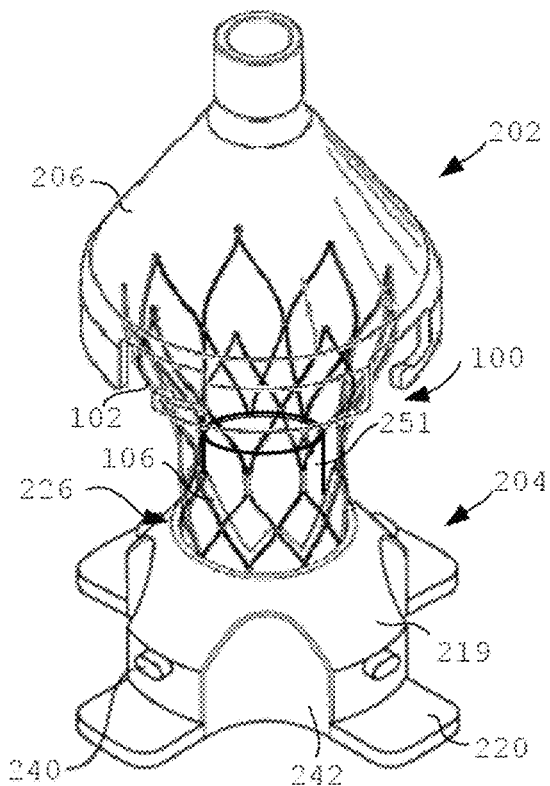
Figure 12:
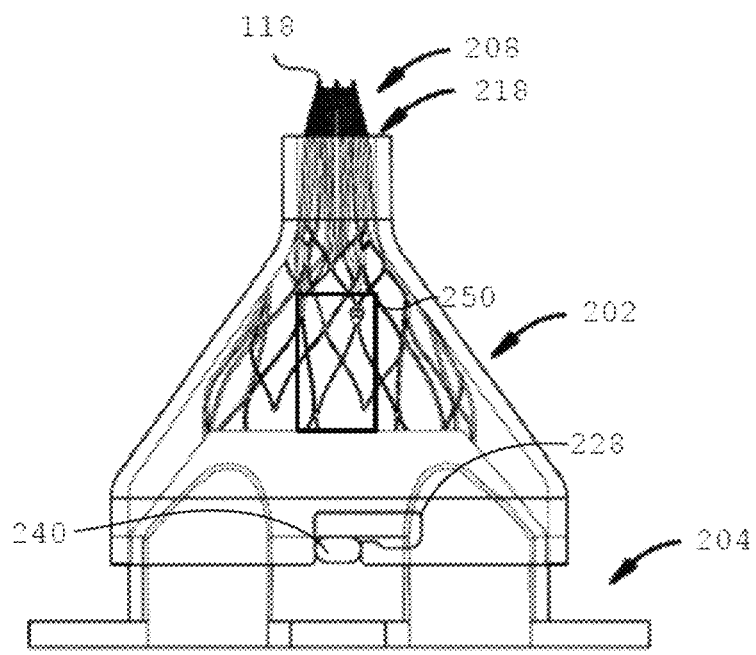
Figure 13:
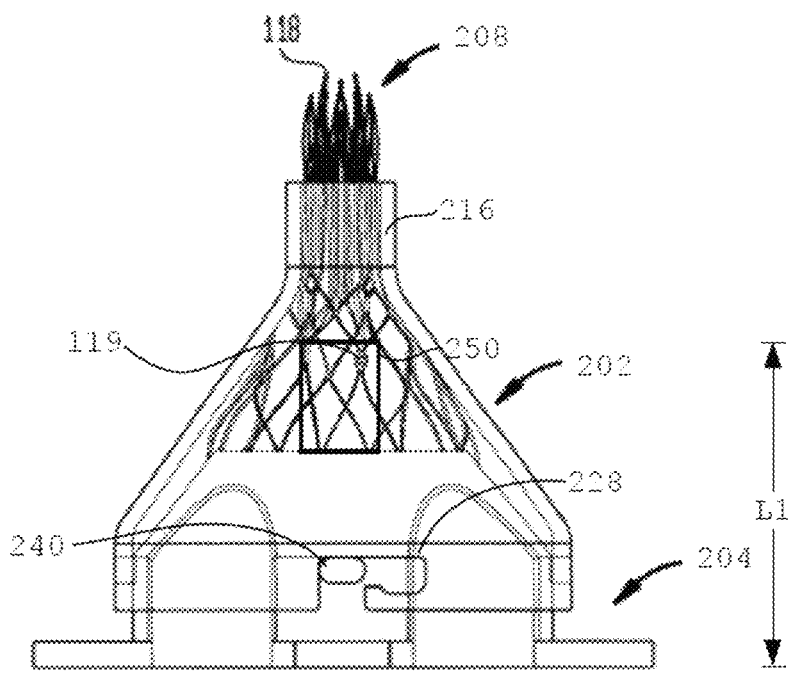

The compression member 202 may then be placed over the aortic section 108 of the stent 102 so that the aortic section of the stent is positioned within the funnel 206, as depicted in FIG. 11. As shown in FIG. 12, the compression member 202 and the support member 204 may then be pushed together, the tapered walls of the funnel 206 gradually compressing the valve 100 until a portion of the aortic section 108 of the stent 102 is forced into and through the opening 218 of the compression member. As valve 100 compresses, leaflets 112 are forced against the outside wall of restrainer 250, but the restrainer prevents the leaflets from coapting with one another. When a portion of the aortic section 108 of the stent 102 passes through the opening 218 of the compression member 202, the retainers 118 of the stent will protrude through the opening 218 and will be positioned closely adjacent to one another. At this point, the pins 240 of the support member 204 will be positioned within the slots 228 of the compression member 202, and the members may be locked together by rotating the support member relative to the compression member, such that the pins 240 of the support member slide toward the closed ends of the slots 228 of the compression member.

With support member 204 and compression member 202 assembled together, restrainer 250 provides a clear passageway 255 through valve 100. In the example shown in FIG. 13, restrainer 250 has a height "L1," such that its first portion 251 extends through the entirety of the annulus section 106 of valve 100. In some examples, the height of restrainer 250 may be selected such that its first portion 251 extends higher than commissure regions 119 of valve 100 when the valve is properly seated within recess 226. Alternatively, the height L1 of restrainer 250 may be chosen such that first portion 251 extends to and contacts the smaller diameter end of funnel 206, or extends through tubular extension 216 if the tubular extension has a large enough diameter.

Figure 14A:
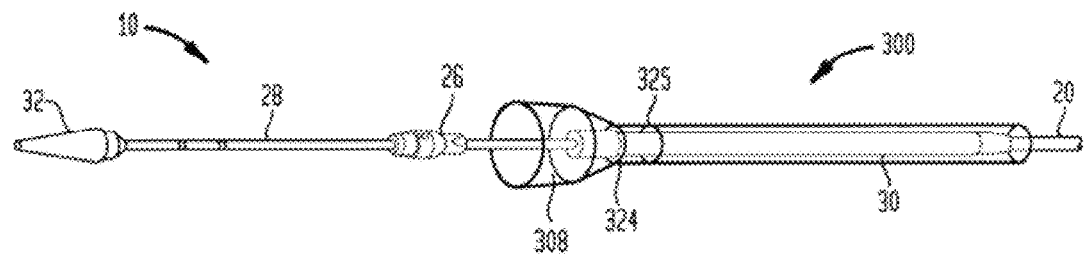

As seen in FIG. 14A, with the distal sheath 30 in a proximal or open position, the constricting member 300 may be placed over the delivery device 10 with the enlarged head 308 positioned closer to the tip 32 than to the hub or handle of the delivery device, and with the distal end 21 of the distal sheath 30 longitudinally positioned between indicator lines 324 and 325 of the constricting member. It will be appreciated that the constricting member 300 also may be placed over the delivery device 10 with the distal sheath 30 in the distalmost or closed position, and that the distal sheath subsequently may be moved to the proximal or open position.

Figure 14B:
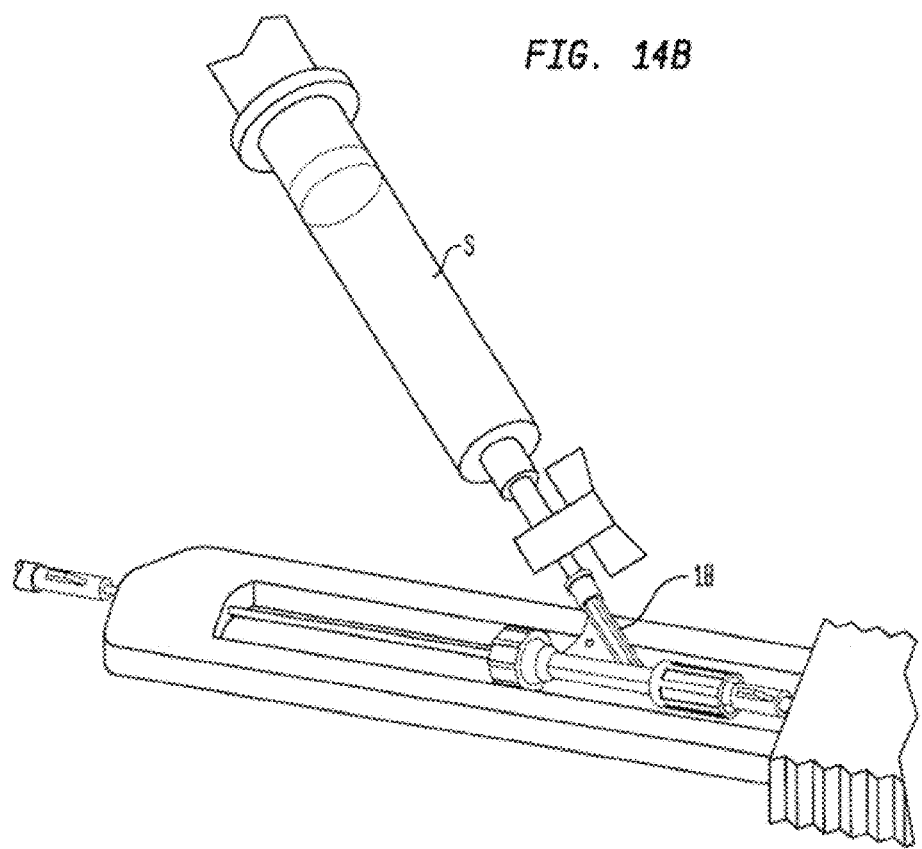

Before loading the valve 100 into the delivery device 10, it is preferable to subject the delivery device to a deairing process. In that regard, with the constricting member 300 assembled over the distal sheath 30 and the distal sheath in an open position, a syringe S may be connected to the Y-connector 18 of the delivery device 10, as shown in FIG. 14B. The syringe may be used to inject a sterile liquid, such as saline, into the proximal end of the delivery device and out through the open compartment 23, thereby flushing the air from the device. During this flushing step, the distal end of the delivery device may be tapped multiple times to facilitate the air removal.

Once flushing of the delivery device 10 has been completed, the tip 32 and the support shaft 28 of the delivery device 10 may be inserted into the end of the collapsed valve 100 protruding from the opening 218 of the compression member 202. To accomplish this, the compression member 202 and the support member 204 may be squeezed closer together. (The dimension of the slots 228 in the longitudinal direction, i.e., the height of the slots, is greater than the dimension of the pins 240 in the longitudinal direction, i.e., the height of the pins. Therefore, even though the compression member 202 and the support member 204 are assembled together, they still may move further toward one another.) As the compression member 202 and the support member 204 move closer together, a greater portion of the stent 102 is forced out through opening 218, causing the retainers 118 to begin to separate from one another. The tip 32 and support shaft 28 of the delivery device 10 may then be inserted between the retainers 118 and into the end of the collapsed valve, as shown in FIG. 15. Tip 32 may also pass through passageway 255 of restrainer 250, which pushes leaflets 112 out of the way of the tip as will be illustrated in greater detail with reference to FIGS. 21A-B.

Figure 16:
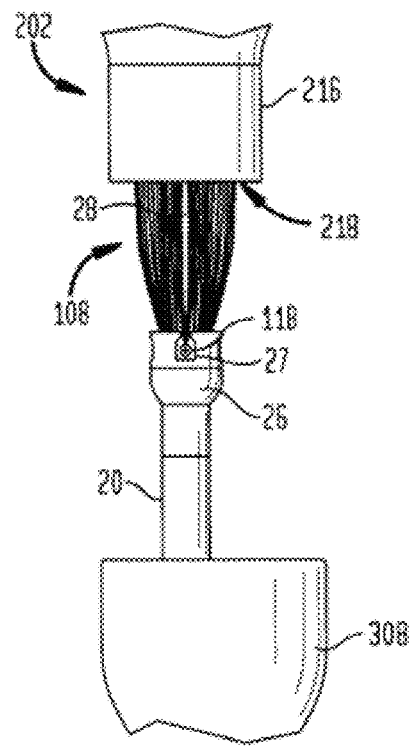
Figure 17:
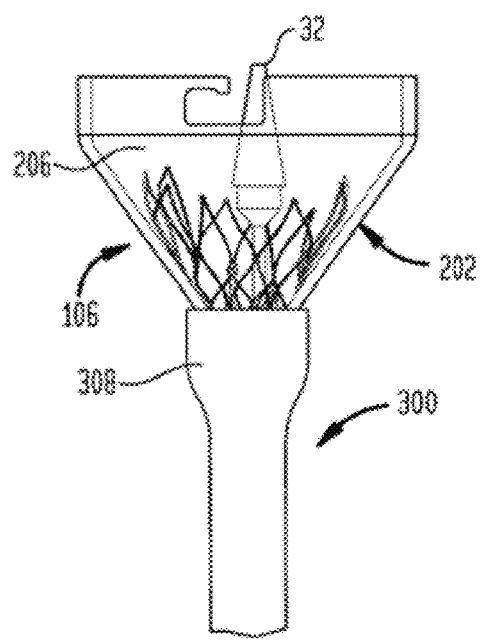

The partial loading assembly 201 then may be advanced along the support shaft 28 until the retainers 118 of the stent 102 are positioned over the retaining element 26 of the delivery device 10. The partial loading assembly 201 may be twisted as needed to align the retainers 118 with the recesses 27 in the retaining element 26. Positioning the retainers 118 within the recesses 27 of the retaining element 26 attaches the stent 102 to the delivery device 10, as seen in FIG. 16. With the stent 102 attached to the retaining element 26, the constricting member 300 and the distal sheath 30 may be slid together toward the partial loading assembly 201 (or the inner tube 16 may be moved proximally relative to the constricting member 300 and the distal sheath 30) to the position in which the distal sheath covers the retainers 118 of the stent, at the same time maintaining the distal end 21 of the distal sheath between indicator lines 324 and 325. The tapered inner surface 312 of the enlarged head 308 facilitates the compression of the stent 102 as it moves into the constricting member 300 (FIG. 17). When the constricting member 300 and the partial loading assembly 201 are close together, they may be joined to one another by assembly of the enlarged head 308 of the constricting member 300 to the tubular extension 216 of the compression member 202.

In order to deair the valve 100, a sterile liquid, such as saline, may be dispensed into the compression member 202 through its first open end 208. To do so, the support member 204 may be disassembled from the compression member 202 by first rotating the support member relative to the compression member, such that the pins 240 of the support member slide toward the open ends of the slots 228 of the compression member. This action unlocks the members from one another. The support member 204 may then be moved away from the compression member 202 to disassemble the partial loading assembly 201. With the first open end 208 of the funnel 206 facing up, the sterile liquid may be dispensed into the compression member 202 through the first open end. The sterile liquid may be dispensed into the compression member 202, such as through a syringe or a sterile container, until the funnel 206 is substantially filled. The syringe may need to be refilled several times during the injection process in order to fill the funnel 206 with the sterile liquid.

Any air bubbles in the sterile liquid within the funnel 206 may then be removed. It is important that little or no air be released into the human body during deployment and/or resheathing of the valve within the human heart, as the air may block vascular flow and cause tissue damage. For this reason, it is important to remove air bubbles from the delivery device 10 and the valve 100 before introducing them into the body. Testing has shown that, if the methods and assemblies described in this application are employed, minimal air will be released into the patient's bloodstream during valve deployment and resheathing.

Figure 18:
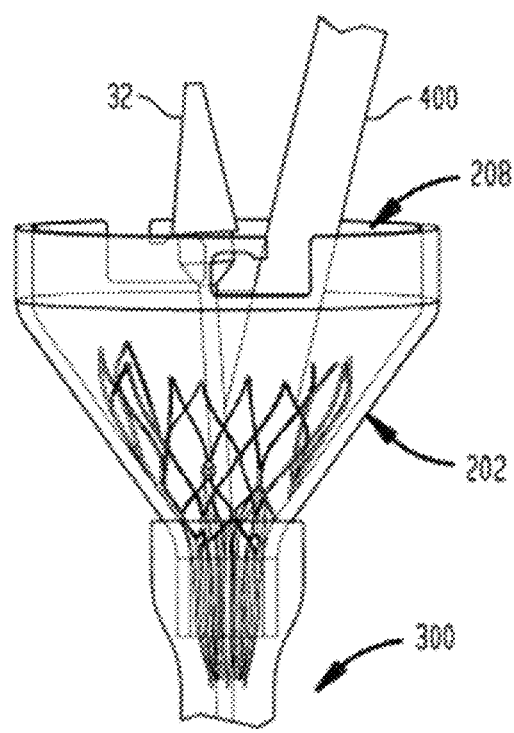
Figure 19:
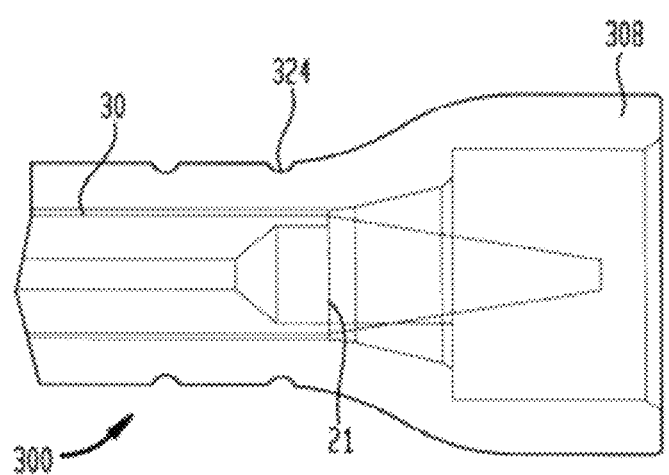

Air bubbles formed in the sterile liquid near the space between the leaflets 112 and the cuff 114 of the valve 100 may be removed by using a tube or rod 400 or any other suitable atraumatic probe. The tube 400 is commonly known in the art as a "leaflet tester" and may be formed of a substantially soft material, such as a soft polymer. In order to remove the air bubbles from the sterile liquid, the tube 400 may be placed into the sterile liquid contained in the funnel 206 of the compression member 202 and used to probe areas of potential air entrapment, including gently agitating the liquid, as shown in FIG. 18. A syringe may be used to remove the air bubbles from the space near the retaining element 26 of the delivery device 10. To do so, the syringe may be inserted into the space near the retaining element 26, and the sterile liquid near the retaining element 26 may be gently agitated with the syringe. After the air bubbles have been removed, the valve 100 may be pulled into the distal sheath 30 until the valve is completely covered. The constricting member 300 and the compression member 202 may then be removed from the delivery device 10. The inner tube 16 of the delivery device 10 may then be flushed with any suitable sterile liquid using, for example, a syringe. To flush the inner tube 16, a syringe may be connected to the hemostatic valve near the hub 14 of the delivery device 10, and then sterile liquid may be injected into the inner tube using the syringe.

In an alternate method of loading the valve 100 into the delivery device 10 and preparing same for use in a patient, the air bubbles may be removed from the distal sheath 30 by submerging the distal sheath, the compression member 202, and the constricting member 300 in a container holding sterile liquid, such as saline. Additional sterile liquid may be injected into the delivery device 10 through the Y-connector 18 using a syringe, as discussed above. The distal sheath 30 of the delivery device 10 may then be shaken and gently tapped against a hard surface to remove air bubbles from the valve 100. The valve 100 may then be pulled into the distal sheath 30, as discussed above.

In view of the tight fit between the collapsed valve 100 and the distal sheath 30, significant friction forces must be overcome in order to move the distal sheath 30 completely over the valve 100. To facilitate this procedure, the stent 102 may be substantially cooled, which, depending on the materials forming the stent, may enable the stent to more easily deform. Thus, once more than about one-half of the length of the stent 102 has been covered by the distal sheath 30, a cold liquid, such as saline solution, may be applied to the stent through the compression member 202 and the constricting member 300. This may be accomplished by removing the support member 204 from the compression member 202 and holding the remainder of the assembly in a substantially vertical orientation with the first end 208 of the funnel 206 facing upwardly. The cold liquid may then be introduced into the compression member 202 using any suitable apparatus. It will, of course, be appreciated that the cold liquid may thus serve two purposes—it may cool the stent 102, and it may serve as the deairing liquid in the deairing procedure described above.

In order for the cooling of the stent 102 to be effective in making it easier for the stent to be completely covered by the distal sheath 30 of the delivery device 10, the stent should be cooled to a temperature below the transition temperature of the material forming the stent. The "transition temperature" of a material is the temperature at which the material changes from one crystal state to another. For the nitinol stents that may be employed in the present invention, a saline solution at about 0° C. may be used. When cooled below its transition temperature, the stent 102 becomes plastic, enabling it to deform much more readily under the forces exerted by the movement of the distal sheath 30 thereover. Accordingly, after the stent 102 has been cooled below the transition temperature, the user may completely cover the stent 102 with the distal sheath 30 of the delivery device 10.

The distal sheath 30 of the delivery device 10 should be non-traumatic. To accomplish this, the distal sheath 30 may be made of soft polymeric material. However, while the valve 100 is loaded into the delivery device 10, the distal end 21 of the distal sheath 30 may slightly expand or flare due to the pressure exerted by the self-expanding stent 102. Since the distal sheath 30 is typically formed from a soft polymer, the distal end 21 of the distal sheath may not return to its original shape once the distal sheath completely covers the valve 100. It is nonetheless important to maintain the original cross-sectional profile of the distal end 21 of the distal sheath 30, because doing so makes the distal sheath more atraumatic and reduces the loading forces required to load the valve 100 into the delivery device 10. In order to maintain the original circular profile of the distal end 21 of the distal sheath 30, the loading assembly 200 preferably includes the constricting member 300 described above.

Figure 20A:
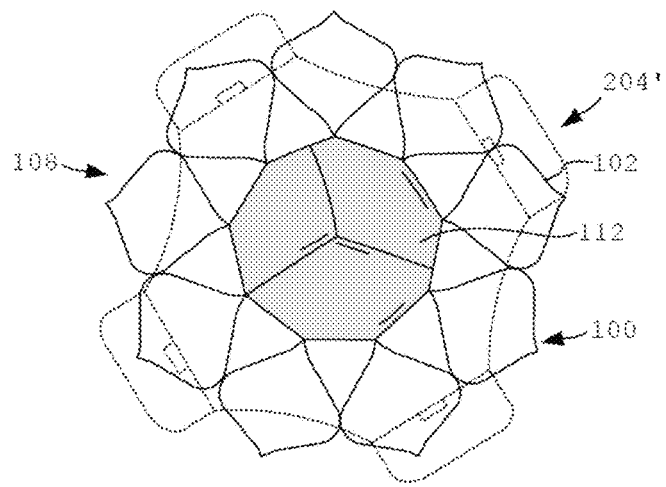
FIGS. 20A-B are top end views of a valve disposed within a support member not having a leaflet restrainer before and after the addition of a compression member, respectively.
Figure 20B:
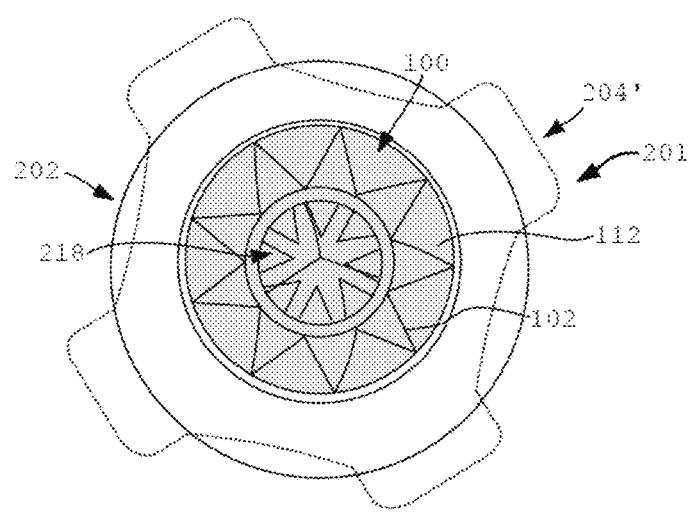

FIG. 20A shows a top view of valve 100 within a support member 204' not having a restrainer 250. Annulus section 106 of valve 100 is disposed within a recess (not shown) of support member 204' while aortic section 108 of stent 102 flares radially outward. At this stage, valve 100 remains in a substantially expanded condition and leaflets 112 of valve 100 coapt with one another as shown. The introduction of compression member 202 as described above collapses aortic section 108 of stent 102 (FIG. 20B). Leaflets 112 remain in a coapting position and collectively obstruct the passage between opening 218 of compression member 202 and the bore (not shown) of support member 204'. Because atraumatic tip 32 of catheter assembly 12 must pass through the center of valve assembly 104 (e.g., between adjacent leaflets 112), leaflets 112 may often interfere with the loading process. Thus, the user may need to physically manipulate one or more of leaflets 112 to remove them from the path of atraumatic tip 32, thereby lengthening the loading time. Additionally, leaflets 112 may become damaged during the loading process as atraumatic tip 32 is advanced through compression member 202 and support member 204'.

Figure 21A:
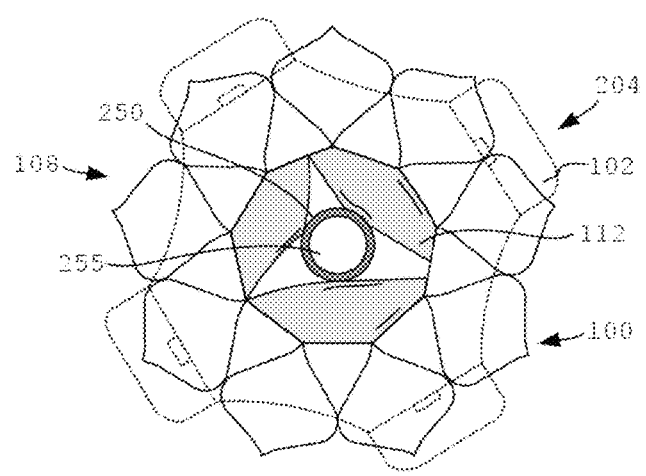
FIGS. 21A-B are top end views of a valve disposed within a support member having a leaflet restrainer before and after the addition of a compression member, respectively.
Figure 21B:
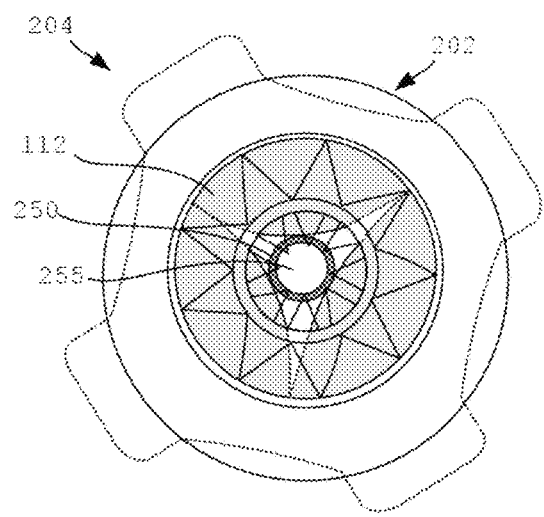

Conversely, restrainer 250 creates a clear path for the delivery device through a valve 100 disposed between a compression member and a support member. FIG. 21A shows a top view of valve 100 within support member 204. Annulus section 106 of valve 100 is disposed within the recess 226 of support member 204 while aortic section 108 of stent 102 flares radially outward. At this stage, valve 100 remains in a substantially expanded condition, but leaflets 112 of valve 100 are separated from one another as they rest against restrainer 250. Thus, passageway 255 of restrainer 250 extends through annulus section 106 of valve 100. As compression member 202 collapses the aortic section 108 of stent 102 (FIG. 21B), leaflets 112 remain parted from one another and valve assembly 104 remains open due to the presence of restrainer 250. Atraumatic tip 32 of catheter assembly 12 may thus pass through passageway 255, without leaflets 112 interfering with the loading process. The inclusion of restrainer 250 deflects leaflets 112 from the center of the loading assembly so that the user does not need to physically manipulate the leaflets 112 to pass atraumatic tip 32 of catheter assembly 12 through the loading assembly. Additionally, leaflets 112 are kept away from the center of the assembly and are thereby safeguarded from possible damage during the loading procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In some embodiments, an assembly for loading a self-expanding prosthetic heart valve into a delivery device, includes a compression member having a longitudinal axis, a first open end with a first diameter, a second open end with a second diameter less than the first diameter, and a wall decreasing in diameter from the first open end to the second open end, the wall defining an open space adapted to receive the valve, a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member, and a substantially tubular restrainer disposed within the support member and, in the operative position of the compression member and the support member, defining a passageway for accepting a portion of the delivery device and leaflets of the valve when the valve is assembled on the support member.

In some examples, the passageway has a substantially constant diameter along the length of the restrainer; and/or the restrainer includes a first portion for restraining the leaflets and a second portion for coupling to the support member; and/or the first portion has a first outer diameter and the second portion has a second outer diameter, the second outer diameter being larger than the first outer diameter; and/or the restrainer is separable from the support member; and/or the restrainer is formed integrally with the support member; and/or the support member recess has a support surface, and the restrainer has a free end spaced from the support surface by a predetermined distance such that commissure regions of the valve are positioned between the support surface and the restrainer free end when the valve is assembled on the support member; and/or the restrainer has a first length, the first length being chosen such that the restrainer extends from the support member toward the compression member and contacts the compression member when compression member and the support member are in the operative position.

In some embodiments, a method for loading a self-expanding prosthetic heart valve into a delivery device includes (a) inserting the heart valve in a support member and about a substantially tubular restrainer, the support member having a longitudinal axis, a base and a recess extending along the longitudinal axis and adapted to receive an end of the valve, and the substantially tubular restrainer defining a passageway configured to obstruct movement of leaflets of the heart valve, and (b) moving the portion of the delivery device through the passageway.

In some examples, the restrainer maintains the leaflets of the heart valve in a substantially open position; and/or the method further includes advancing the heart valve through a compression member until the at least one retainer protrudes from an open end of the compression member.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An assembly for loading a self-expanding prosthetic heart valve into a delivery device, comprising:
   a compression member having a longitudinal axis, a first open end with a first diameter, a second open end with a second diameter less than the first diameter, and a wall decreasing in diameter from the first open end to the second open end, the wall defining an open space adapted to receive the valve;
   a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member; and
   a substantially tubular restrainer having a second portion disposed within the support member and a first portion extending beyond the support member and, in the operative position of the compression member and the support member, defining a passageway for accepting a portion of the delivery device and maintaining leaflets of the valve in an open position when the valve is assembled on the support member.

2. The assembly according to claim 1, wherein the passageway has a minimum diameter along the length of the restrainer that is capable of receiving a portion of the delivery device.

3. The assembly according to claim 1, wherein the second portion is for coupling to the support member.

4. The assembly according to claim 3, wherein the first portion has a first outer diameter and the second portion has a second outer diameter, the second outer diameter being larger than the first outer diameter.

5. The assembly according to claim 1, wherein the restrainer is separable from the support member.

6. The assembly according to claim 1, wherein the restrainer is formed integrally with the support member.

7. A method for loading a self-expanding prosthetic heart valve into a delivery device, comprising:
inserting the heart valve in a support member and about a substantially tubular restrainer, the support member having a longitudinal axis, a base and a recess extending along the longitudinal axis and adapted to receive an end of the valve, and the substantially tubular restrainer defining a passageway configured to maintain leaflets of the heart valve in an open position; and
moving the portion of the delivery device through the passageway.

8. The method of claim 7, wherein the restrainer maintains the leaflets of the heart valve in a substantially open position.

9. The method of claim 7, further comprising advancing the heart valve through a compression member until the at least one retainer protrudes from an open end of the compression member.

10. An assembly for loading a self-expanding prosthetic heart valve into a delivery device, comprising:
a compression member having a longitudinal axis, a first open end with a first diameter, a second open end with a second diameter less than the first diameter, and a wall decreasing in diameter from the first open end to the second open end, the wall defining an open space adapted to receive the valve;
a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member; and
a substantially tubular restrainer disposed within the support member and, in the operative position of the compression member and the support member, defining a passageway for accepting a portion of the delivery device and leaflets of the valve when the valve is assembled on the support member,
wherein the support member recess has a support surface, and the restrainer has a free end spaced from the support surface by a predetermined distance such that commissure regions of the valve are positioned between the support surface and the restrainer free end when the valve is assembled on the support member.

11. An assembly for loading a self-expanding prosthetic heart valve into a delivery device, comprising:
a compression member having a longitudinal axis, a first open end with a first diameter, a second open end with a second diameter less than the first diameter, and a wall decreasing in diameter from the first open end to the second open end, the wall defining an open space adapted to receive the valve;
a support member having a longitudinal axis, a base and a recess extending along the longitudinal axis and adapted to receive an end of the valve, the support member and the compression member being movable relative to one another between an initial position in which the base of the support member is relatively far from the first open end of the compression member and an operative position in which the base of the support member is relatively close to the first open end of the compression member; and
a substantially tubular restrainer disposed within the support member and, in the operative position of the compression member and the support member, defining a passageway for accepting a portion of the delivery device and leaflets of the valve when the valve is assembled on the support member,
wherein the restrainer has a first length, the first length being chosen such that the restrainer extends from the support member toward the compression member and contacts the compression member when compression member and the support member are in the operative position.

* * * * *